(12) United States Patent
Hartlep et al.

(10) Patent No.: US 7,769,438 B2
(45) Date of Patent: Aug. 3, 2010

(54) METHOD AND DEVICE FOR DETERMINING THE LOCATION OF ELECTRICAL ACTIVITY OF NERVE CELLS

(75) Inventors: Andreas Hartlep, Naring (DE); Christoph Pedain, München (DE)

(73) Assignee: BrainLAB AG, Feldkirchen (DE)

( * ) Notice: Subject to any disclaimer, the term of this patent is extended or adjusted under 35 U.S.C. 154(b) by 1329 days.

(21) Appl. No.: 11/249,730

(22) Filed: Oct. 13, 2005

(65) Prior Publication Data

US 2006/0149217 A1    Jul. 6, 2006

Related U.S. Application Data

(60) Provisional application No. 60/623,067, filed on Oct. 28, 2004.

(30) Foreign Application Priority Data

Oct. 15, 2004    (EP)    .................................. 04024685

(51) Int. Cl.
*A61B 5/04* (2006.01)

(52) U.S. Cl. ........................ 600/544; 600/545; 604/503; 604/66

(58) Field of Classification Search ......... 600/544–547, 600/410–411, 416, 424; 604/66, 65, 502–504
See application file for complete search history.

(56) References Cited

U.S. PATENT DOCUMENTS

| | | | | |
|---|---|---|---|---|
| 4,503,863 A | * | 3/1985 | Katims | ........................ 600/554 |
| 4,909,261 A | * | 3/1990 | Rothenberg | .................. 600/547 |
| 5,263,488 A | * | 11/1993 | Van Veen et al. | ............. 600/544 |
| 5,687,724 A | * | 11/1997 | Jewett et al. | .................. 600/409 |
| 5,735,814 A | * | 4/1998 | Elsberry et al. | ................ 604/43 |
| 6,061,587 A | | 5/2000 | Kucharczyk et al. | |
| 2003/0093005 A1 | | 5/2003 | Tucker | |
| 2004/0009459 A1 | * | 1/2004 | Anderson et al. | ........... 434/262 |
| 2004/0138551 A1 | | 7/2004 | Hartlep et al. | |

FOREIGN PATENT DOCUMENTS

EP    1 398 641 A1    3/2004

OTHER PUBLICATIONS

Wieringa et al., "Processing MRI Data for Electromagnetic Source Imaging", Nov. 1993, Medical & Biological Engineering & Computing, pp. 600-606.
European Search Report for European Application No. 04 02 4685 dated Mar. 23, 2006.

* cited by examiner

*Primary Examiner*—Robert L Nasser
*Assistant Examiner*—Michael D'Angelo
(74) *Attorney, Agent, or Firm*—Renner, Otto, Boisselle & Sklar, LLP

(57) ABSTRACT

A method and device for determining the location of electrical activity or hyperactivity of nerve cells in an anatomical structure of a body, wherein an electrical conductivity model of the anatomical structure is generated and electrical impulses are detected by at least one electrode. Using the model and the detected electrical impulses, the location or locations of the electrical activity in the anatomical structure are determined.

20 Claims, 2 Drawing Sheets

METHOD AND DEVICE FOR DETERMINING THE LOCATION OF ELECTRICAL ACTIVITY OF NERVE CELLS

RELATED APPLICATION DATA

This application claims priority of U.S. Provisional Application No. 60/623,067 filed on Oct. 28, 2004, which is incorporated herein by reference in its entirety.

FIELD OF THE INVENTION

The present invention relates to electrical activity or hyperactivity of nerve cells and, more particularly, to a method and device for determining the location or range of electrical or hyperactivity in the brain.

BACKGROUND OF THE INVENTION

A method for treating neurodegenerative diseases is known from U.S. Pat. No. 5,735,814, wherein a sensor is implanted into the brain of a patient and the electrical potentials detected by sensor electrodes are used to regulate the administration of a substance into the brain.

SUMMARY OF THE INVENTION

A method for determining the location or range of electrical activity or hyperactivity of nerve cells in a body is provided. More particularly, electrical signals that can be emitted from one or more cells, such as cells in areas of activity in the brain, can be detected by at least one, and preferably two, three, four or more electrodes that can be implanted in the body. The electrodes can be implanted into a particular anatomical structure such as, for example, the brain or the spinal cord, or can be applied to the body or structure. The electrodes can be formed and positioned as described in U.S. Pat. No. 5,735,814, the contents of which is hereby incorporated by reference in its entirety.

In order to determine the location or range of the electrical activity, the electrical activity need not necessarily be situated at the detection location of a sensor or electrode. The electrical signals or fields can originate from nerve cells or centers of activity that can be situated away from the actual detection location. To this end, a model of the electrical or specific electrical conductivity of examined anatomical structures, such as a model for describing or simulating the electrical conductivity or electrical resistance of the brain of a patient, can be produced.

The model, in conjunction with the electrical signals or impulses detected at one or more electrodes, can enable the determination of the location or locations of electrical activity or hyperactivity. It is thus possible not only to measure the electrical signals in the immediate vicinity of electrodes or sensors and/or assign measured electrical signals to the immediate vicinity of the electrodes or sensors, but also to calculate or simulate how electrical signals have spread out from a center of activity up until being detected by the respective electrodes or sensors. The simulation can be conducted using the produced model of the electrical conductivity and/or resistance or using a simulation of the conductivity of the brain substance, for example. In determining the spread of electrical signals from a center of activity, one or more locations or ranges of electrical activity, such as, for example, an epileptic focus in the brain, can be determined by absolute or relative location or range values, without an electrode having to be positioned at these locations. Thus, using a model of the electrical conductivity or the electrical resistance of the examined body structure, the location of electrical activity of brain cells can be precisely determined.

Generally, patient-specific data can be used in order to determine the model of the general or specific electrical conductivity or resistance, such as, for example, MR-DT (magnetic resonance degrees twaddle) images. Via MR-Dt, for example, the density or ion concentration of a liquid, in particular brain liquid, can be ascertained, to produce a patient-specific three-dimensional model of the anatomical and/or physiological characteristics (e.g., the electrical conductivity of the brain). Ultrasound, computer tomography (CT), PET, MRI, SPECT recordings or other measurement methods or data capture methods such as, for example, biopsy, also can be used to ascertain general or electrical brain characteristics. For example, the anatomical structure of the brain or the dispersion and conductivity of liquids in the brain can be obtained using one of the above recording techniques. Furthermore, so-called generic models also can be used, which, for example, describe common electrical parameters such as the specific electrical resistance of nerve cells or other anatomical structures. These generic models can be modified, for example, by an imaging measurement method performed on the patient, to produce a patient-specific three-dimensional model for describing the electrical conductivity of the examined body structure. Thus, body characteristics or tissue characteristics can be generally or individually ascertained that are relevant to the spread of electrical signals. More particularly, specific conductivities or resistances can be determined, calculated or simulated that can have an effect on the spread of an electrical signal in the body structure in question.

If, for example, electrical signals, such as potentials from the vicinity of the sensor, are detected by a sensor to which two or more electrodes are attached at different positions of the sensor, then by using the model for the spread of electrical signals in a body or anatomical structure, it is possible to determine the location of hyperactivity of nerve cells, which can point to an epileptic attack. If, for example, it is established that there are electrical activities that can influence the health or condition of a patient, then electrical signals also can be emitted via electrodes introduced into the body and, in particular, into the brain, that can be identical to the signals detected by the measurement electrodes. The electrical signals can suppress or weaken possible effects of the detected electrical activities, such that, for example, an epileptic attack can be identified while still developing, and suppressed. In order to determine the nature of the signals emitted by the electrodes introduced into the body, in particular their impulse sequence and energy, the model for determining the spreading capacity of electrical signals (e.g., a model for three-dimensionally describing the electrical conductivity) can be used, such that, for example, electrical signals administered by means of one, two, three or more electrodes can be emitted such that hyperactivity of brain cells or neurones can be suppressed or weakened in a desired area of the body or brain.

The information obtained can be used to determine the location or locations of electrical activity, to enable, for example, the introduction of a liquid or substance into the body or brain, so as to alter the physiological or electrical characteristics of the brain. With respect to introducing substances into a body and in particular into the brain by means of a catheter and, in particular, by using an implantable pump, wherein electrical signals are used to control dispensing the substance, reference is made to the teaching of U.S. Pat. No. 5,735,814.

Furthermore, the effect of administering one or more substances on the electrical conductivity or electrical resistance of the body structure in question can be simulated, and the simulation results can be taken into account in the subsequent treatment, particularly when calculating a model of the three-dimensional electrical conductivity, for example.

The data ascertained using the method described above for determining the location of the areas of electrical activity or hyperactivity can be relayed or communicated to a known navigation system. The navigation system then can assist in positioning one or more electrodes, catheters or pumps at particular areas, which, for example, may be particularly advantageous for emitting signals or dispensing substances to diseased areas of the body, such as areas with hyperactive neurons.

Furthermore, the invention provides a computer program which, when it is loaded onto a computer or is running on a computer, can perform a method as described above. The invention also provides a program storage medium or a computer program product comprising such a program.

The invention also provides a device for determining the location of electrical activity of nerve cells includes a data input device that, for example, can be connected to a data capture unit, such as a magnetic resonance tomograph, a computer tomograph, or the like. The input or captured, generic or patient-specific data can be communicated to a computational unit or computer that is capable of evaluating the data, such as image data, for example. The computational unit or computer also can obtain from a database, for example, anatomical data with respect to the electrical conductivity, degree of electrical sensitivity or electrical absorption or anatomical information, regarding the distribution of white and grey matter.

The computational unit can include a conventional computer, a neural network and/or a fuzzy logic, for example, in order to ascertain patient-specific parameters, such as the electrical conductivity of the tissue or the dispersion of a liquid in the tissue. The parameters can be ascertained from a data set such as, for example, measurement results of a data capture unit for individually examining a body or a tissue structure, and can be used to produce a model for describing the electrical conductivity of a body structure. Furthermore, the computational unit can simulate the dispersion of a fluid, the concentration of a fluid, or the chemical properties of one or more fluids in the body region in question, such as for example in the brain. The simulation can be conducted using the generic or patient-specific information, wherein general biological parameters, anatomical parameters or functions can be added from a database as generic data.

Furthermore, the computational unit can be connected to at least one electrode or sensor, from which electrical impulses or potentials of areas of the patient, such as the brain, for example, can be detected, to identify one or more locations from which the electrical activity or hyperactivity has emanated. The one or more locations can be identified using the three-dimensional model for describing the specific electrical conductivity or resistance. In particular, using the model, it is possible to calculate, from the intensity and/or nature of the electrical signals or potentials detected by an electrode, the distance from the electrode of the center of activity which emitted said electrical signals. If two, three or more electrodes are used, then by using the anatomical model for describing the electrical conductivity, it is possible to calculate, relatively precisely, the locations of one or more areas in the body which emitted the electrical signals detected by the electrode or electrodes.

A device in accordance with the invention preferably includes electrodes for emitting signals, one or more catheters, pumps for dispensing a substance in doses, and/or a navigation system. The navigation system can be used to position the electrodes, catheters and pumps. Further, the execution and/or success of a treatment of the areas of hyperactive nerve cells supplied by a substance and/or via the application of electrical potentials can be monitored. If an actual course of treatment deviates from a planned or simulated course of treatment (e.g., a treatment for suppressing hyperactivity of nerve cells), then one or more treatment parameters, such as, for example, electrical impulses administered via electrodes, can be modified with regard to their intensity or impulse forms, or parameters for administering substances for influencing the electrical conductivity can be modified.

DETAILED DESCRIPTION

Figure 1:
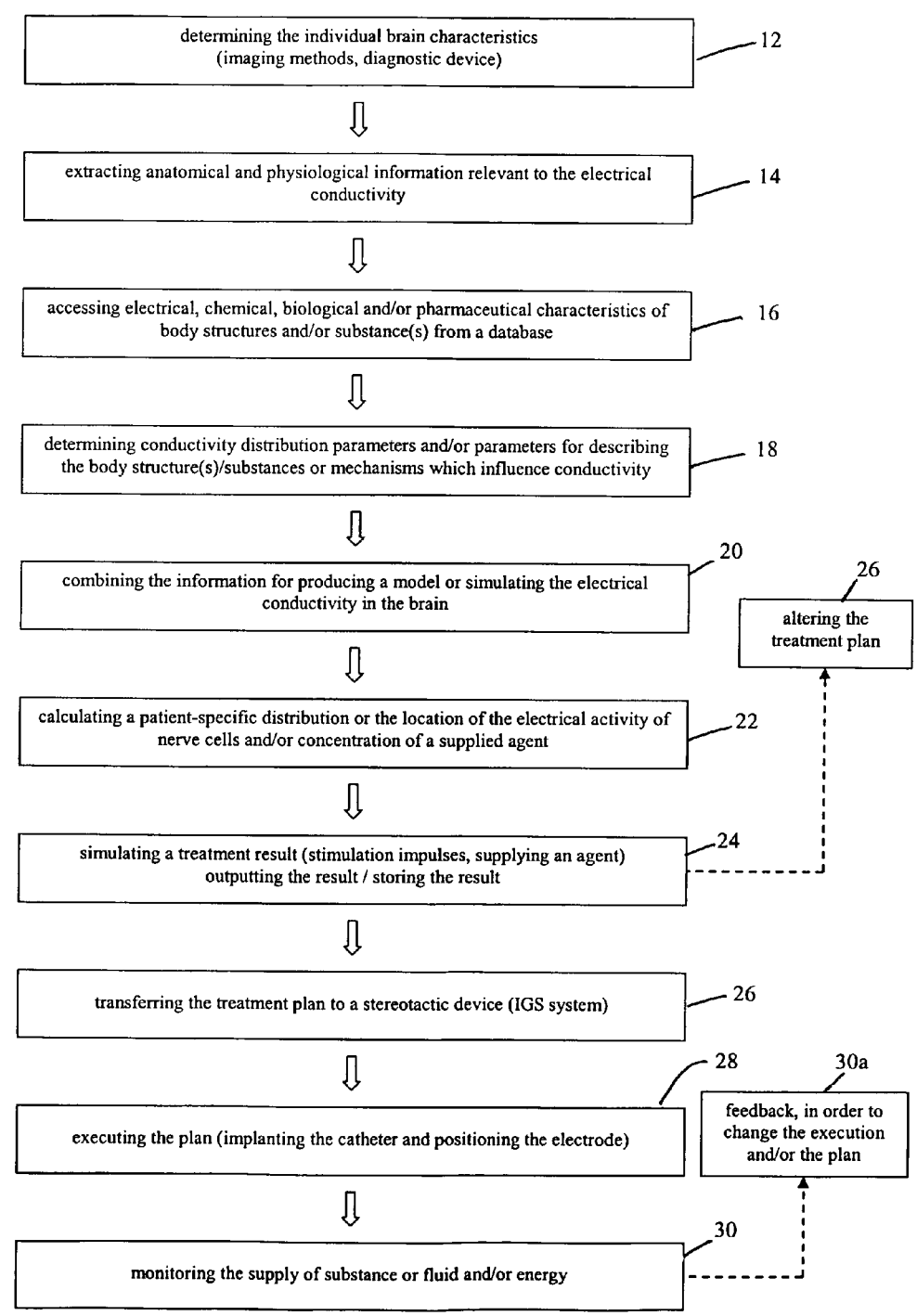
FIG. 1 is a flow diagram illustrating an exemplary method for determining the location of electrical activity in nerve cells in accordance with the invention.

FIG. 1 shows a flow chart 10 of a method for determining the location or range of electrical hyperactivity in accordance with an embodiment of the invention. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

In accordance with the method, the individual brain characteristics or brain parameters are determined patient-specifically at step 12, to which end, for example, known imaging methods can be used, such as magnetic resonance tomography, ultrasound, computer tomography, PET, SPECT, biopsy or other known methods to capture the characteristics and/or parameters. The captured data for describing characteristics of the brain are then evaluated, in order to obtain relevant anatomical, physiological and/or functional information as indicated at step 14. To this end, a generic model, for example, can be used. Alternatively, known mathematical models for ascertaining specific characteristics relevant to the dispersion of a substance or to the absorption or conduction of energy, can be used in conjunction with the captured data. In particular, the (specific) electrical conductivity, thermal diffusibility, course of nerve tracts, density distribution, elasticity, liquid content, blood content, blood flow values, vascular permeability or other information for describing characteristics or structures of the brain can be used. If, for example, patterns known from a generic model or general information are used, then characteristics of the brain can be estimated for particular volumes or areas of the brain (assuming they have not been or cannot be ascertained directly by measurement).

The information ascertained by measurement and/or a generic model, or from a database, which may be relevant to the method in accordance with the invention, can be one or more of the following mechanisms or characteristics:

- transport mechanism in the body (for example for bodily liquids or externally administered liquids or substances);
- discharge or dispersion of a liquid in the body or tissue (dependent inter alia on the permeability or on physiological characteristics, such as the blood-brain barrier, for example);
- hydraulic and/or chemical and/or biological characteristics at body structure boundaries (e.g., blood-brain barrier, sulci);
- diffusion that has an effect on the transport mechanism of a substance in the tissue;
- electrical conductivity;
- degree of energy sensitivity;
- degree of energy absorption;
- anatomical information (white/grey matter).

If, using one or more of the characteristics or mechanisms described above, a model of the brain or of the body region to be treated has been produced for describing the electrical conductivity, then a local distribution or the spread and weakening of electrical signals in the brain can be simulated. The simulation can be used to track the electrical signal back from a measurement electrode to its location of origin. For the simulation, electrical but also general chemical (ion concentration), biological and/or pharmaceutical characteristics of the body structure or of an administered substance can be obtained, for example, from a database as indicated at step 16. Additionally, one or more of the following types of information or characteristics can be adduced at step 18 to simulate the conductivity distribution or the spreading mechanism of electrical signals:

- information with respect to the administration parameters of a substance (such as for example local administration in tissue or systemic administering, the duration of administration or infusion, the effect of the metabolism (metabolisation) on the active substance or the carrier mechanism or carrier substance, the arrangement of the supply devices such, as for example, catheters and pumps);
- measured, assigned and/or determined electrical characteristics of the anatomical area or tissue;
- pharmaceutical characteristics of the respective agent (e.g., heat-sensitive liposomes, energy-emitting or particle-emitting liquids, radiation sensitizers, toxins, etc.);
- arrangement and/or characteristics of the electrode(s);
- mathematical model that uses the aforementioned information, from which a dispersion of the liquid and/or a dose can be calculated.

Furthermore, parameters regarding the energy supply and information with respect to the device or mechanisms by which the electrical energy is supplied are used to simulate the supply of electrical energy or signals into the target tissue. To simulate the supply of energy, and in particular to calculate the signal to be applied (strength, signal form), one or more of the following types of information can be used:

- measured or assigned characteristics of the target area;
- information regarding the arrangement of the electrodes or concentration of substances, objects or liquids which have an effect on the energy sensitivity parameters and/or absorption parameters of the target area;
- positional information on the electrical energy-emitting objects or liquids;
- emission characteristics of the objects or liquids;
- time parameters regarding the arrangement or dispersion of the objects or liquids;
- energy administering parameters from sources arranged outside the target area;
- a mathematical model which uses the information above and can determine a local dispersion of the energy supply.

At step 20, the simulation results described above are combined. In other words, the effect the simulated administration of electrical energy (e.g., in accordance with a treatment plan for supplying energy in different doses using various electrodes) has in various areas or regions of the body is ascertained, taking into account the conductivity model or the simulated dispersion of one or more substances or liquids in a tissue or body structure. It is then possible, for example, to determine whether centers of hyperactivity can be reached and/or influenced in a sufficient amount using the treatment plan data used for the simulation. The treatment plan data can include, for example, the location of an electrode or catheter for introducing a substance and a calculated signal form or characteristic dispensing curve of the substance. The characteristic dispensing curve can describe the course over time of an amount of substance that is dispensed, or pressure at which the substance is introduced into the tissue. Further, mechanisms for supplying energy also can be taken into account.

The calculated patient-specific arrangement of the electrodes, the signal forms to be applied, the concentration of the introduced substance, the dispersion of the substance or liquid and/or the distribution of energy are calculated at step 22, wherein the result can be output (e.g., on a video display) and stored (e.g., in computer memory).

It is possible to simulate the reaction of the target area (e.g., of the center of hyperactivity) over time as indicated at step 24, wherein the parameters for describing tissue behavior also can be altered over time. This can be used to describe the dynamic behavior of the target area, such that, for example, effects on the tissue arising from the treatment (e.g., from the supplied electrical signals, the administered substance or the supplied energy) can be taken into account in planning the treatment.

A data set ascertained by a computational unit using the method described above can be output, for example graphically, in order to display one or more of the following types of information:

- distribution of the sources of electrical signals, dispersion of the administered substances and/or carrier substances of the substances or medicines;
- locally varying concentration of the substances and/or carrier substances which influence the electrical characteristics of the tissue, for example;
- distribution of energy in the tissue in the case of conductive or energy-emitting substances;
- distribution of energy of an external energy source;
- distribution of energy, taking into account the effect of the administered electrical energy, liquids or substances which alter the energy absorption and/or energy sensitivity of the target area (effect distribution).

If, after simulating, it is established that a desired or predetermined treatment result is not achieved or not completely achieved, then at step 24a the method can be performed iteratively. More specifically, treatment parameters such as, for example, the dosing or the administration mechanisms of the externally supplied electrical energy (location of the electrodes; duration, strength, course over time of the electrical signals), substances or liquids, or the mechanisms for supplying energy, are altered and a new simulation is performed using the altered initial parameters until a satisfactory simulation result is obtained.

If the simulation result is satisfactory, then at step 26 the treatment plan can be transferred to a stereotactic device such as an image-guided surgery (IGS) system or the like, and at step 28 the treatment plan can be executed and one or more electrodes and/or catheters can be positioned at the points ascertained by the simulation as being favorable.

In addition, the supply of the liquid, substance and/or electrical energy can be measured or monitored at step 30 while the treatment is performed. This can provide a user feedback as to whether the treatment plan is being correctly performed or should be changed (e.g., whether parameters for supplying the substance or a liquid or for supplying the electrical energy should be adjusted or altered in order to obtain an improved treatment result), as indicated at step 30a.

Figure 2:
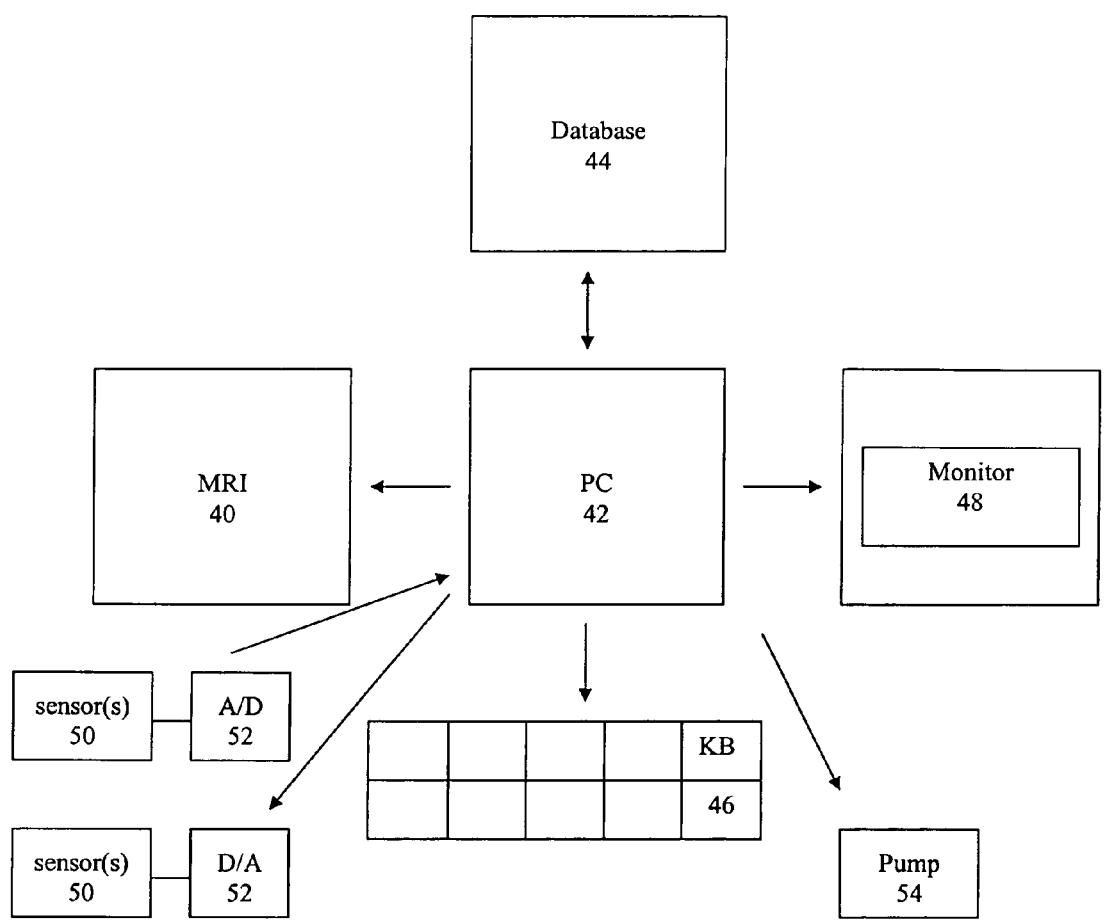
FIG. 2 is a schematic diagram of an exemplary device that can be used to determine the location of electrical activity in nerve cells in accordance with the invention.

FIG. 2 shows an exemplary device for determining the location of electrical activity of nerve cells, wherein a magnetic resonance tomograph 40 captures patient-specific data and outputs the data to a computational unit 42. The computational unit 42 is connected to a database 44 in which a generic model for describing the three-dimensional electrical conductivity distribution of the area of the body detected by the magnetic resonance tomograph 40 is stored. The computational unit 42 forms a model of the conductivity distribution of the body structure from the data transmitted from the magnetic resonance tomograph 40 and the database 44. The model describes the patient-specific parameters regarding the distribution or spread of electrical signals generated in or supplied to the body structure.

Further data with respect to the type of a substance to be administered or the type of the electrical energy supplied, for example, can be input to the computational unit 42 by a user via an input unit such as a keyboard 46 or the like. The computational unit 42 can access additional information from the database 44 with respect to physical, chemical or physiological characteristics of the substance or the electrodes used, for example, in order to perform the method described above. The simulation results ascertained by the computational unit 42 can be displayed graphically on a monitor 48.

One or more sensors 50 are connected to the computational unit 42 via an analog-to-digital converter A/D 52 and, for example, can be introduced into the brain of a patient and provide detected electrical signals to the computational unit 42, to determine the location of the origin of the electrical signals. In order to treat brain dysfunctions, one or more electrodes, which also can be identical to the described sensors 50, can be connected to the computational unit 42 via a digital-to-analog converter D/A, in order to emit electrical signals for treating brain dysfunctions. Furthermore, a pump 54 such as described in U.S. Pat. No. 5,735,814 can be connected to the computational unit.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a location of electrical activity or hyperactivity of nerve cells in an anatomical structure of a body, comprising:

generating an electrical conductivity model of the anatomical structure;

detecting electrical signals via at least one input electrode;

using the electrical conductivity model and the detected electrical signals to determine a location or locations of the electrical or hyper activity in the anatomical structure; and outputting electrical signals to the anatomical body structure via at least one output electrode, wherein the intensity and/or form of said output signals is ascertained using the electrical conductivity model.

2. The method as set forth in claim 1, wherein generating the electrical conductivity model includes using patient-specific data to generate the electrical conductivity model.

3. The method as set forth in claim 2, wherein using patient specific data includes using an imaging method to obtain the data.

4. The method as set forth in claim 1, wherein generating the electrical conductivity model includes using generic data to generate the electrical conductivity model.

5. The method as set forth in claim 1, further comprising using a pump to dispense a substance into the anatomical structure, wherein the pump is controlled in accordance with the location or locations of the electrical activity in the anatomical structure.

6. The method as set forth in claim 1, further comprising communicating parameters that describe the location of electrical activity in the anatomical structure to a navigation system, wherein the navigation system provides data for positioning one or more electrodes and/or catheters on or in the body.

7. A computer readable medium comprising computer executable instructions adapted to perform the method as set forth in claim 1.

8. The method as set forth in claim 1, wherein outputting electrical signals includes outputting electrical signals via electrodes introduced into the body.

9. The method as set forth in claim 1, wherein outputting electrical signals includes setting and intensity and/or form of the outputted signals such that the outputted signals suppress or weaken effects of electrical or hyperactivity of brain cells or neurons in the determined location or locations of the anatomical structure.

10. The method as set forth in claim 9, wherein the intensity and/or impulse of the output signals correspond to input signals provided by the at least one input electrode.

11. The method according to claim 1, further comprising implanting the at least one output electrode within the anatomical body structure.

12. A device for determining the location of electrical activity of nerve cells in a body or in body tissue, comprising:

a data capture unit configured to detect patient-specific parameters of the body or body tissue, wherein said parameters can be used to describe an electrical conductivity of the body or body tissue;

a computational unit operatively coupled to the data capture unit, wherein said computational unit is configured to obtain the patient-specific parameters from the data capture unit;

a database accessible by the computational unit, wherein said database includes data for describing electrical characteristics of a particular type of tissue or a particular body structure, data for describing mechanisms for spreading electrical signals and/or data for describing the effect on the electrical conductivity of the body structure or tissue of a substance, said computational unit being configured to retrieve and/or store said data in the database and to generate an electrical conductivity model of the body or body tissue based on the data stored in the database and the patient-specific parameters;

at least one input electrode operatively coupled to the computational unit, wherein said input electrode can detect electrical signals, and the computational unit assigns the detected electrical signals to one or more locations or areas of the body or body tissue based on the electrical conductivity model of the body or body tissue; and at least one output electrode operatively coupled to the computational unit, said output electrode operable to emit electrical signals to the body, wherein the intensity and/or form of the emitted signals is ascertained using the electrical conductivity model.

13. The device as set forth in claim 12, comprising a data output unit, wherein a result of assigning the signals or to the calculated location of nerve cell activity data is graphically displayed.

14. The device as set forth in claim 12, further comprising at least one pump for dispensing a predefined amount of a substance onto or into the body or body tissue.

15. The device as set forth in claim 12, further comprising at least one navigation system operatively coupled to the computational unit, said navigation system configured to position or direct the positioning of electrodes, catheters or pumps in or in the vicinity of areas of electrical activity or hyperactivity.

16. The device according to claim 12, wherein the computational unit is configured to set an intensity and/or form of the emitted signals such that the emitted signals suppress or weaken effects of electrical or hyperactivity of brain cells or neurons in the determined location or locations of the anatomical structure.

17. A program embodied in a computer-readable medium for determining a location of electrical activity or hyperactivity of nerve cells in an anatomical structure of a body, comprising:

code that generates an electrical conductivity model of the anatomical structure;

code that detects electrical signals via at least one input electrode;

code that uses the electrical conductivity model and the detected electrical signals to determine a location or locations of the electrical or hyper activity in the anatomical structure; and code that directs the generation of electrical signals to a location inside the anatomical body structure via at least one output electrode, wherein the intensity and/or form of said generated signals is ascertained using the electrical conductivity model.

18. The program according to claim 17, further comprising code that directs the generation of the electrical signals such that an intensity and/or form of the generated signals suppresses or weakens effects of electrical or hyperactivity of brain cells or neurons in the determined location or locations of the anatomical structure.

19. A system for determining a location of electrical activity or hyperactivity of nerve cells in an anatomical structure of a body, comprising:

a processor circuit having a processor and a memory;

an electrical activity sub-system stored in the memory and executable by the processor, the electrical activity sub-system comprising:

logic that generates an electrical conductivity model of the anatomical structure;

logic that detects electrical signals via at least one input electrode;

logic that uses the electrical conductivity model and the detected electrical signals to determine a location or locations of the electrical or hyper activity in the anatomical structure; and logic that directs the generation of electrical signals to a location inside the anatomical body structure via at least one output electrode, wherein the intensity and/or form of said generated signals is ascertained using the electrical conductivity model.

20. The system according to claim 19, further comprising logic that directs the generation of the electrical signals such that an intensity and/or form of the generated signals suppresses or weakens effects of electrical or hyperactivity of brain cells or neurons in the determined location or locations of the anatomical structure.

\* \* \* \* \*